United States Patent [19]

Pope et al.

[11] Patent Number: 4,553,549
[45] Date of Patent: Nov. 19, 1985

[54] ORAL ORTHOPEDIC/ORTHODONTIC APPLIANCE FOR TREATING NEUROMUSCULAR IMBALANCE

[76] Inventors: Bryan M. Pope, 709 Hobbs, Jefferson City, Mo. 65101; Richard Hawkins, 4480 Kendall Cir., Gulfport, Miss. 39501

[21] Appl. No.: 659,094

[22] Filed: Oct. 9, 1984

[51] Int. Cl.[4] .............................................. A61N 1/36
[52] U.S. Cl. .................................. 128/421; 128/787; 433/6; 433/7; 433/140
[58] Field of Search ................... 128/207.14, 419 FR, 128/421, 776, 787; 433/6, 7, 140

[56] References Cited

U.S. PATENT DOCUMENTS

| Re. 27,847 | 12/1973 | Jankleson | 433/140 |
|---|---|---|---|
| 1,855,118 | 4/1932 | Rizer et al. | 433/140 |
| 3,259,129 | 7/1966 | Tepper | 128/787 |
| 3,277,892 | 10/1966 | Tepper | 128/787 |
| 3,312,216 | 4/1967 | Wallshein | 128/136 |
| 3,522,805 | 8/1970 | Wallshein | 128/136 |
| 3,871,370 | 3/1975 | McDonald | 128/136 |
| 3,884,226 | 5/1975 | Tepper | 128/136 |
| 4,026,023 | 5/1977 | Fisher | 433/7 |
| 4,112,936 | 9/1978 | Blachly | 128/207.14 |
| 4,170,230 | 10/1979 | Nelson | 128/139 |
| 4,198,967 | 4/1980 | Dror | 128/136 |
| 4,239,487 | 12/1980 | Murdock | 433/7 |
| 4,261,354 | 4/1981 | Nelson | 128/203.23 |
| 4,262,666 | 4/1981 | Nelson | 128/203.23 |
| 4,275,725 | 6/1981 | Nelson | 128/207.14 |
| 4,289,127 | 9/1981 | Nelson | 128/207.14 |
| 4,304,227 | 12/1981 | Samelson | 128/136 |
| 4,416,626 | 11/1983 | Bellavia | 433/7 |
| 4,431,411 | 2/1984 | Witzig et al. | 433/6 |
| 4,433,956 | 2/1984 | Witzig | 433/7 |

OTHER PUBLICATIONS

Cooper and Rabuzzi, "Myofacial Pain Dysfunction Syndrome: A Clincal Study of Asymptomatic Subjects," *Laryngocscope*, vol. 94, No. 1, pp. 68–75, Jan. 1984.

*Primary Examiner*—William E. Kamm
*Attorney, Agent, or Firm*—Hoffmann, Dilworth, Baron & Baron

[57] ABSTRACT

An orthopedic/orthodontic appliance for treating neuromuscular imbalance which interrupts balanced myofacial growth and development which includes mandible fixation means for maintaining the mandible of the user in an essentially neuromuscularly balanced position when the mouth is closed. The appliance also includes a pressure equalization conduit extending from a position exterior the lip seal of the user to a position in the posterior of the oral cavity which is in fluid communication with the pharyngeal cavity so that the pressure in the user's pharyngeal cavity is equalized to the ambient pressure outside the head while the user's mandible is maintained in the essentially neuromuscularly-balanced position.

21 Claims, 5 Drawing Figures

ORAL ORTHOPEDIC/ORTHODONTIC APPLIANCE FOR TREATING NEUROMUSCULAR IMBALANCE

BACKGROUND OF THE INVENTION

The present invention relates to the art of orthopedic-/orthodontic appliances designed to treat various oral dysfunctions and, in particular, those appliances designed to treat maladies resulting whole or in part from oral facial neuromuscular imbalance.

Studies relating to maladies of the head and neck have recently shown that conditions of structure significantly interrelate to neuromuscular balance such that no single discipline of medicine can always fully explain the cause and/or the necessary medical treatment. For example, improper relationship of a person's upper and lower jaw in combination with one or more of several physical conditions can precipitate various disorders such as obstructive sleep apnea, improper tongue position, inefficient swallowing and breathing physiology, as well as several diagnosed dental problems, etc.

It has been known in the art of orthodontics, which is generally considered the specialty of dentistry dealing with the positional irregularities of the teeth, to provide orthopedic/orthodontic apparatus and devices, both fixed and removable, that adjust the position or growth of various parts associated with the structure and function of the oral cavity. Many of such irregularities referred to collectively as malocclusion are characterized by malpositioning of the lower jaw in relation to the maxillary dental arch. In such cases, the lower jaw or mandible and, concomitantly, the mandibular dental arch, depending upon the class of malocclusion, is anterior or posterior to the maxillary arch. Correction of malocclusions has usually involved "stretch reflex" initiated by the introduction of an orthopedic appliance into the patient's mouth which causes the muscles to pull the mandible in the required direction for correction. Corrective procedures can also include expansion of the maxillary arch in order to provide proper lateral occlusion. See U.S. Pat. Nos. 4,433,956; 4,431,411; 4,416,626; and 4,170,230. In the past, determination of the correct occlusive position has to a great extent depended on alignment of the upper and lower teeth without regard for neuromuscularly balanced myofascial condition. Furthermore, corrective movement using such orthopedic devices can be hindered by negative pressure created in the palatal pharyngeal arch.

Other head and neck maladies related and unrelated to orthodontics have required further types of apparatus to provide symptomatic relief and/or remedial treatment. For example several types of breathing devices have been developed to prevent problems associated with incorrect human air passages such as mouth breathing, improper tongue position, obstructive sleep apnea, dysphagia and dysphasia, etc. Devices of this type are generally designed to relieve the blocked breathing airways, but are usually not provided with corrective treatment features which are directed to long term relief and/or cure of the malady. Samples of such devices are disclosed in U.S. Pat. Nos. 4,289,127; 4,275,725; 4,262,666; and 4,261,354 to Nelson, as well as U.S. Pat. No. 4,304,227 to Samelson.

Various derivative conditions such as tongue thrust, etc., have also promulgated treatment apparatuses designed to alleviate the isolated condition. See, for example, U.S. Pat. Nos. 3,277,892 and 3,259,129 for their disclosure of devices employing an electrical charge to prevent or reduce tongue thrust, and U.S. Pat. Nos. 3,884,226, and 3,871,370 which show palate approximating mechanisms designed to minimize tongue thrust. Refer also to U.S. Pat. No. 3,522,805 to Wallshein for its disclosure of a dental appliance designed to inhibit tongue-thrusting and thumb-sucking.

As a result of recent investigations into various head and neck problems, such as myofascial pain dysfunction, sleep disorders, vallecular dysphagia, globus hystericus, etc., dental and medical investigators are beginning to realize the tremendous interdependence of their respective technologies and methods of treatment for resolving many of the head and neck maladies. In particular, efforts have been made to make interrelated diagnostic studies and integrate the data in order to advance corrective action and apparatus to treat all the conditions associated with the malady.

To this end the present invention has as its objective, provision of a multi-functional orthopedic/orthodontic appliance which gives symptomatic relief to various maladies of the head and neck by corrective adjustment of neuromuscular conditions, et al. contributing to the particular malady.

SUMMARY OF THE INVENTION

The present invention is an orthopedic/orthodontic appliance for treating neuromuscular imbalance which interrupts balanced myofascial growth and development including a mandible fixation means for maintaining the mandible of the user in an essentially neuromuscularly balanced position when the mouth is closed. The appliance also includes at least one pressure equalization conduit which extends from a position exterior the seal formed by closed lips to a position in the oral cavity which is in fluid communication with the pharyngeal cavity. As a result of this appliance the pressure in the users pharyngeal cavity is equalized to the ambient pressure outside the users oral cavity while the users mandible is manintained in an essentially balanced neuromuscular position. In the preferred embodiment of the invention the mandible fixation means can be a palatal covering having occlusal biting surfaces into which the teeth of the user fit in an essentially neuromuscularly balanced closed position. The occlusal biting surfaces can be anterior biting surfaces, posterior biting surfaces or both anterior and posterior biting surfaces.

In another preferred embodiment the palatal covering can be made of moveable segments which are connected by actuation means that can be actuated to move the segments of the palatal covering away from each other. This is done, of course, to provide corrective forces which can spread maxillary segments of the user. Usually, such segments can be actuated by means of connecting jackscrews.

In a further preferred embodiment of the above appliance, the palatal covering can include baffles attached to the sides of the covering and extending toward the interior of users mouth so that the inter occlusal space between the users teeth is covered when the mouth is closed, so that the users tongue is prevented from thrusting between the users teeth when the mouth is closed. Preferably, such baffles can be made to be articulable with respect to the palatal covering so that the user can collapse the baffles while inserting them into the mouth and thereafter extend them to the operative condition. A still further preferred embodiment would include baffles which are removeable from the palatal covering.

Referring to all embodiments of the invention, it is contemplated that the at least one conduit can be a flexible hollow tube preferably having an inside diameter of at least from about 2 to about 3 millimeters so that appropriate pressure equalization can be achieved. In one preferred embodiment there can be two of such tubes. The tube material can be generally any useable non-toxic, and preferably inexpensive material, such as polyethylene.

Construction of the appliance which provides appropriate pressure equalization conduit positioning includes tube holders along one side edge of the palatal covering so that a tube can be attached thereby along the exterior of the side edge at a distance therefrom so that the tube extends along the outside surface of the teeth around the posterior of the teeth to the position which is in communication with the pharyngeal cavity. Alternatively, the pressure equalization conduit can be an air passage integral with the palatal covering extending from the desired position to a connecting position, usually at the anterior portion of the palatal covering, and also a tube carrying means at the connecting position which is adapted to receive a hollow tube and carry such tube in fluid communication with the air passage and extends the tube forward of the palatal covering. In this latter embodiment the ambient atmosphere is in fluid communication with the desired position in the mouth when the mouth is closed. Preferably the tube carrying means is a rigid tubular insert extending from the palatal covering and having an outside diameter sufficiently large to stretch the plastic tube so that the tube is maintained thereon by the force of friction. Such a tube can conveniently have an outside diameter of from 2 to about 3 millimeters while the plastic tube can be a polyethylene tube having an inside diameter of from about 2 to about 3 millimeters just so long as the inside diameter of the tube is slightly less than the outside diameter of the insert.

The present invention is also directed to a method for treating neuromuscular imbalance which hinders balanced myofascial growth and development which includes establishing a neuromuscularly balanced rest position of the subject's mandible when the mouth is closed, maintaining the mandible in such a position while equalizing the pressure in the oral-pharyngeal cavity to the ambient pressure outside the user's head so that orthodontic and orthopedic adjustments are facilitated. The method of attaining this condition can be implemented by application of transcutaneous electrical neuro stimulation to the area of the notch between the coronoid process and the condylar head of the mandible.

In one embodiment, such stimulation can include electrical pulses of not more than about 25 milliamps which are applied for about 500 microseconds at a rate of about 40 pulses per minute until electrical activity levels in the masseter and temporalis muscles in the resting mandibular position achieves a level of not more than about 10 microvolts. The mandible can be maintained in such a balanced position by providing an orthopedic appliance which holds the mandible in the established position.

Furthermore, the pressure can be equalized by providing a conduit from the outside of the lipseal formed by the closed mouth of the user to a position in the mouth of the user which is in fluid communication with the oral-pharyngeal cavity.

As a result of the present invention, many maladies of the head and neck can be provided with symptomatic relief as well as corrected by propagation and maintenance of a physiological balance between all bodily governing systems located therein, e.g., musculoskeletal, neuromuscular as well as dento-osseous systems.

In particular, included in the group of disorders which can be effectively relieved and treated are obstructive sleep apnea, muscle spasm of the Fifth and Seventh cranal nerve groups which can be connected to speech disorders as well as swallowing disorders, increasing lateral development of the maxillary arch, alignment of the maxillary anterior teeth as well as correction of posterior cross-bite, correction of tongue disfunction in swallowing, increase in oral volume which enhances physiological function of breathing, speaking, deglutition and facial contour.

For a better understanding of the present invention, together with other and further objects, reference is made to the following description, taken in conjunction with the accompanying drawings and its scope will be pointed out in the appended claims.

BRIEF DESCRIPTION OF THE DRAWINGS

Preferred embodiments of the invention have been chosen for purposes of illustration and description and are shown in the accompanying drawings, wherein.

DETAILED DESCRIPTION OF THE DRAWINGS

Figure 1:
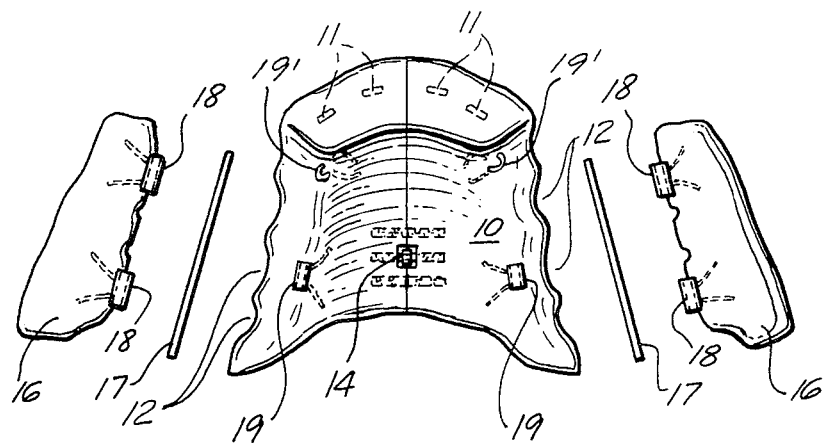
FIG. 1 is a view of the bottom of one embodiment of the present invention which has been exploded to show all of the component parts.

Referring to the drawings, there is shown in FIG. 1 the major portion of an orthopedic appliance according to the present invention which has been exploded to show the different parts. Specifically, the portion of the appliance which fits into the patient's palate is indicated as a palatal covering 10 which can be, as shown herein, composed of two separate halves connected along a medial line generally corresponding to the maxillary suture of the patient's mouth. This portion is generally made of acrylic and is molded to conform to the patient's mouth, using established techniques of a dental laboratory. In one such technique, a plaster cast is made of the patient's mouth and dentition. The palatal portion of the appliance is fabricated to the shape of the plaster cast. Required clasps or fixation means which will be described hereinbelow, are embedded in the acrylic at the time of molding.

In order to prepare the palatal covering required in the apparatus of the present invention, it is necessary to first take the mold of the patient's upper and lower dentition and register the bite when the teeth are in a neuromuscularly balanced position. Such a position can be measured in many different ways, such as by electrical activity, i.e., electromyography, muscle coordination, clinching ability as well as smooth mandibular movement and optimal occlusal position relative to efficient mastication. Basically, it has been found that such position can be achieved using technology related to determining healthy neuromuscular conditions, such as that reported by Cooper and Rabuzzi, "Myofacial Pain Disfunction Syndrome: A Clinical Study Of Asymptomatic Subjects," *LARYNGOSCOPE*, Vol. 94, pp. 68-75, January 1984, the contents of which are included herein by reference.

Once the patient has achieved a neuromuscularly balanced position with regard to the mandible and maxillary arch, e.g., that is wherein muscle output is 10 microvolts or less in the resting position, four muscles have equal work output and the mandibular motion is smooth and rapid, the appropriate registration should be taken such that upon closing the mouth the teeth of the user are forced into the balance position. These registrations can be both anterior impressions 11 or posterior impressions 12, or both. Generally, the healthy position of the mandible in relationship to the cranium is achieved by application of transcutaneous electrical neurostimulation (TENS) to the Vth and VIIth cranial nerves by placing surface electrodes in the area of the notch between the coronoid process and the condylar head of the mandible. This provides for soft tissue electrical conduction of the stimulus to the inner sides of the mandible where the Vth nerve exits the scull as well as the superficial VIIth nerve. Pulses can be applied up to about 25 milliamps for 500 microseconds at a fixed rate of 40 pulses per minute to relax the muscles. As a result of this application, electrical activity levels in the masseter and temporalis muscles in the resting mandibular position were at healthy levels of 10 microvolts or less and can be achieved in about 60 minutes. In any event, after the palatal covering has been prepared, it can be provided with expansion means such as jackscrews 14, which can connect lateral halves and/or anterior and posterior portions (not shown in the drawings herein). Such elements or combinations of them can be used to cause buccal, protractional, distal, rotational, or lingual movement of the individual teeth or groups of teeth while the dominant effect of the orthopedic appliance is at work.

Referring still to FIG. 1 there is also shown detachable side baffles 16 which can be attached by means of pins 17 to the bottom of palatal covering 10 by use of connectors 18, 19, and 20. The connectors 19 and 20 are imbedded in the acrylic palatal covering 10 and the connectors 18 are imbedded in the acrylic material of their respective baffles 16. It should be noted that FIG. 1 does not show the entire invention in that it does not include the pressure equalization conduit, but does show a basic mandible maintaining vehicle, i.e., palatal covering 10, with its associated options.

In the remainder of the drawings, similar features have been indicated with the same numbers as in FIG. 1 in order to be consistent.

Figure 2:
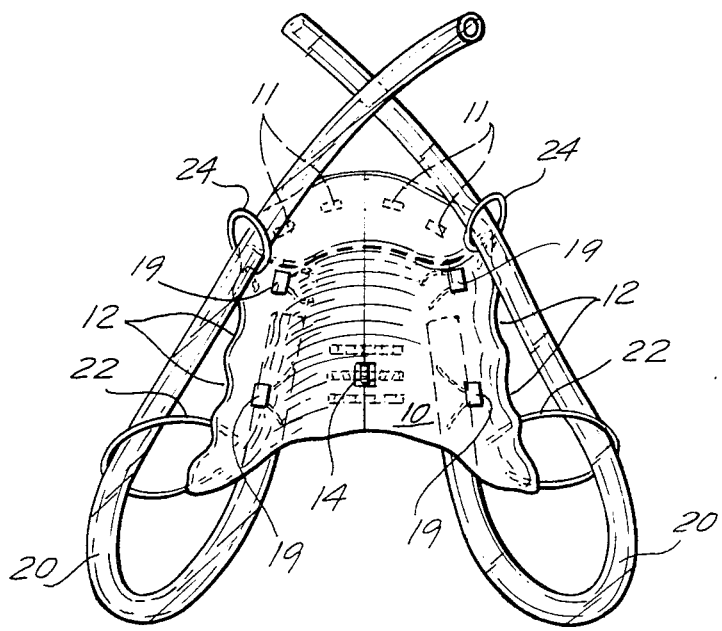
FIG. 2 is a plan view of the top of an apparatus of the present invention.

Referring to FIG. 2, there is depicted an embodiment of the present invention having mandible holding feature, palatal covering 10 having teeth impressions 11 and 12, which is provided with tubular members 20 as pressure equalization conduits. Specifically, the tubes 20 which are preferably of polyethylene material are connected to the palatal covering 10 by means of wire holders 22 and 24 which are secured to the acrylic palatal covering by being imbedded therein during the formation of the covering. Inasmuch as the view of FIG. 2 is from the top of the palatal covering which is secured directly to the user's palate, the portion of the tubes 20 which are secured to the covering are seen in phantom, and are attached to the palatal covering so that they terminate at position within the palatal arch at a position which is fluid communication with the oral-pharyngeal cavity. As a result of this pressure equalization conduit, the compromised nasal pharyngeal airway can be relieved providing a symptomatic relief to obstructive sleep apnea and/or dysphagia as well as relieving negative pressure or the partial vacuum created by the lipseal and ineffective eustachian tube function. Furthermore, as a consequence of the relief of negative pressure, forces designed to exert expansive pressure against the mid-palatal suture as well as parts of the palate and teeth are very effective.

Figure 3:
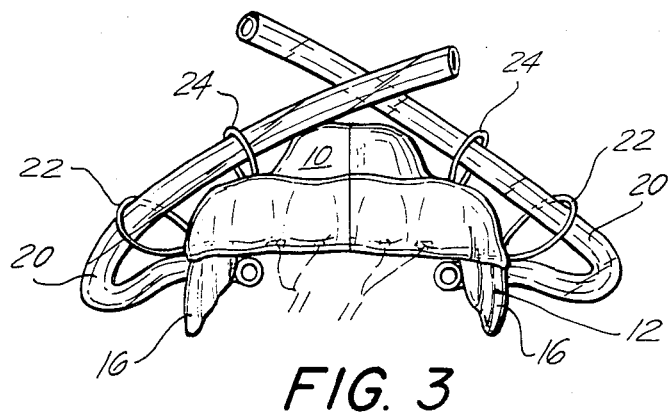
FIG. 3 is a front view of an apparatus of the present invention similar to the one shown in FIG. 2.

In FIG. 3 there can be seen a front view of the apparatus as shown in FIG. 2 with the added feature of side baffles 16 connected to the palatal covering 10. Furthermore, the palatal covering 10 shown in FIG. 3 has two parts so that it can be expanded when provided with a connective jackscrew as shown in FIG. 1. In operation, the arched portion of the palatal covering 10 is fitted in the maxillary of the patient with the top portion fitted against the palate of the user while the anterior block 30 fits against the anterior teeth, the lower anterior teeth fitting into the impressions 11 as shown in FIG. 1.

Figure 4:
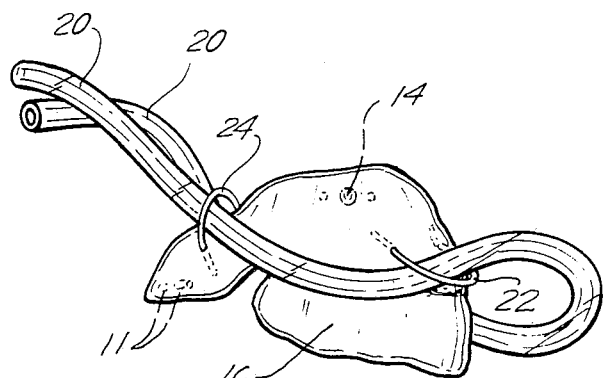
FIG. 4 is a side view of an apparatus of the present invention as shown in FIG. 3.

Referring to FIG. 4, there can be seen an elevated side view of the embodiment shown in FIG. 3 wherein tube 20 is extended along the side of the palatal covering 10 at a distance from the side of the covering such that it fits on the outside of the teeth of the user between the teeth and the inside of the gum, and extends around the posterior of the maxillary teeth and thence into the palatal cavity. Side baffles 16 are shown in the extended position to prevent the tongue of the user from being thrust between the teeth during swallowing.

Figure 5:
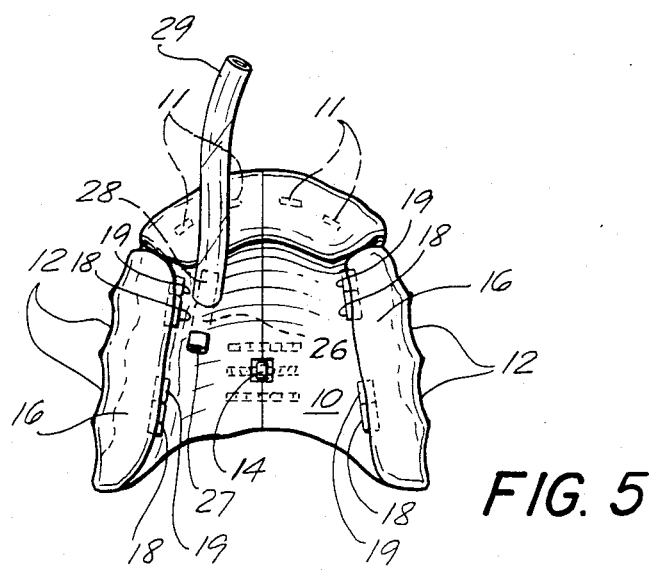
FIG. 5 is a bottom view of a different embodiment of the present invention similar to those shown in FIGS. 3 and 4.

Finally, in FIG. 5 there can be seen yet another embodiment of the present invention in which a conduit 26 integral to the palatal covering 10 is provided with an extension 28 used as a connector for tube 29. In this way, the pressure equalization conduit is provided through the front of the device into the integral conduit 26 and thence out the exit port 27. Referring to the side baffles 16 it can be seen in this drawing that one of the baffles is in the operative position on the left hand side while the right hand baffle is collapsed inwardly. Usually, the user will want to have both of the side baffles in the collapsed position during insertion into the mouth, and then raise them into the upright position after putting them in the mouth.

Thus while there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

We claim:

1. An orthopedic/orthodontic appliance for treating neuromuscular imbalance which results in interruption of balanced myofascial growth and development comprising:

mandible fixation means which maintains the mandible of the user in an essentially neuromuscularly-balanced position when the mouth is in the closed position, and at least one pressure equalization conduit which extends from a position exterior the seal formed by closed lips to a position in the oral cavity which is in fluid communication with the oral-pharyngeal cavity, whereby the pressure in the user's oral-pharyngeal cavity is equalized to the ambient pressure outside the user's oral cavity while the user's mandible is maintained in said essentially balanced neuromuscular position.

2. The appliance of claim 1 wherein said mandible fixation means comprises a palatal covering having occlusal biting surfaces into which the teeth of the user fit in the neuromuscularly-balanced position when the mouth is closed.

3. The appliance of claim 2 wherein said occlusal biting surfaces are one of anterior biting surfaces, posterior biting surfaces, and both anterior and posterior biting surfaces.

4. The appliance of claim 2 wherein said palatal covering further comprises moveable segments and actuation means connected for actuating between said segments which can be actuated to move said segments of said palatal covering away from each other.

5. The appliance of claim 4 wherein said actuation means comprises expansion jackscrews.

6. The appliance of claim 2 wherein said palatal covering further comprises baffles attached to the sides of said covering and extended therefrom toward the interior of the user's oral cavity so that the inter occlusal space between the user's teeth is covered when the mouth is closed whereby the user's tongue is prevented from thrusting between the user's teeth when the mouth is closed.

7. The appliance of claim 6 wherein said baffles are articulable with respect to said palatal covering.

8. The appliance of claim 7 wherein said baffles are removeable from said palatal covering.

9. The appliance of claim 1 wherein said at least one conduit is a flexible hollow tube.

10. The appliance of claim 9 wherein said tube has an inside diameter of from about 2 to about 3 mm.

11. The appliance of claim 10 wherein there are two of said tubes.

12. The appliance of claim 9 wherein said tube is polyethylene.

13. The appliance of claim 9 wherein said palatal covering further comprises tube holders along one side edge of said covering and said tube is attached thereby along an exterior of said one side edge of said palatal covering at a distance therefrom so that said tube extends along the outside surface of the teeth and around the posterior of the teeth to said position which is in fluid communication with the oral-pharyngeal cavity.

14. The appliance of claim 1 wherein said pressure equalization conduit comprises an air passage integral with said palatal covering extending from said posterior position to a connecting position on said covering, and tube carrying means at said connecting position which is adapted to receive a hollow tube and carry said tube in fluid communication with said air passage and extended forward of said palatal covering whereby the ambient atmosphere is in fluid communication with said posterior position when the mouth is closed.

15. The appliance of claim 14 wherein said tube carrying means is a rigid tubular insert extending from said palatal covering a sufficient length to slide a hollow tube thereover, said rigid tubular insert having an outside diameter sufficiently large so that said tube is maintained thereon by the force of friction.

16. The appliance of claim 15 wherein said insert has an outside diameter of from about 2 to 3 mm and said plastic tube is a polyethylene tube having and inside diameter of from about 2 to 3 mm and is slightly less than the outside diameter of said insert.

17. A method for treating neuromuscular imbalance which hinders balanced myofacial growth and development comprising:
    establishing neuromuscularly-balance rest position of the subjects mandible when the mouth is closed,
    maintaining the mandible in said position, and
    equalizing the pressure in the oral-pharyngeal cavity to the ambient atmospheric pressure outside the user's head whereby orthodontic and orthopedic adjustments are facilitated.

18. The method of claim 17 wherein said balanced position is established by application of transcutaneous electrical neural stimulation to the area of the notch between the coronoid process and the condylar head of the mandible.

19. The method of claim 18 wherein said stimulation comprises electrical impulses of not more than about 25 ma. and for about 500 $\mu$sec. at a rate of about 40 pulses per minute until electrical activity levels in masseter and temporalis muscles in the resting mandibular position achieved a level of not more than about 10 uv.

20. The method of claim 17 wherein said mandible is maintained in said balanced position by providing an orthopedic appliance which holds said mandible in the established position.

21. The method of claim 17 wherein said pressure is equalized by providing a conduit from outside the lip seal formed by the closed mouth of the user to a position in the mouth which is in fluid communication with the oral-pharyngeal cavity.

* * * * *